US012569543B2

(12) United States Patent
Hoejbjerg

(10) Patent No.: US 12,569,543 B2
(45) Date of Patent: Mar. 10, 2026

(54) SEMAGLUTIDE IN CARDIOVASCULAR CONDITIONS

(71) Applicant: Novo Nordisk A/S, Bagsvaerd (DK)

(72) Inventor: Oluf Kristian Hoejbjerg, Vaerloese (DK)

(73) Assignee: NOVO NORDISK A/S, Bagsvaerd (DK)

( * ) Notice: Subject to any disclaimer, the term of this patent is extended or adjusted under 35 U.S.C. 154(b) by 0 days.

(21) Appl. No.: 16/097,032

(22) PCT Filed: Apr. 28, 2017

(86) PCT No.: PCT/EP2017/060160

§ 371 (c)(1),
(2) Date: Oct. 26, 2018

(87) PCT Pub. No.: WO2017/186896

PCT Pub. Date: Nov. 2, 2017

(65) Prior Publication Data

US 2019/0134162 A1 May 9, 2019

(30) Foreign Application Priority Data

Apr. 28, 2016 (EP) .................................... 16167458
Sep. 12, 2016 (EP) .................................... 16188262

(51) Int. Cl.
*A61K 38/26* (2006.01)
*A61P 3/10* (2006.01)
*A61P 9/10* (2006.01)

(52) U.S. Cl.
CPC ................ *A61K 38/26* (2013.01); *A61P 3/10* (2018.01); *A61P 9/10* (2018.01)

(58) Field of Classification Search
CPC ...... A61K 38/00; A61K 39/3955; A61K 9/08; A61P 9/00; A61P 3/10; C07K 16/40; C12N 2310/351
See application file for complete search history.

(56) References Cited

U.S. PATENT DOCUMENTS

| | | | | |
|---|---|---|---|---|
| 8,129,343 | B2 | 3/2012 | Lau et al. | |
| 9,186,392 | B2 * | 11/2015 | Klein | A61K 38/2278 |
| 9,278,123 | B2 * | 3/2016 | Sauerberg | A61K 9/2013 |
| 9,968,659 | B2 | 5/2018 | Rasmussen | |
| 2003/0119734 | A1 * | 6/2003 | Flink | A61P 3/00 514/7.2 |
| 2003/0220255 | A1 | 11/2003 | Knudsen et al. | |

FOREIGN PATENT DOCUMENTS

| | | | | |
|---|---|---|---|---|
| CL | 2017002538 | | 4/2018 | |
| IL | 184051 | | 8/2015 | |
| JP | 2008-533105 | A | 8/2008 | |
| WO | 03084563 | A1 | 10/2003 | |
| WO | 2005049061 | A2 | 6/2005 | |
| WO | WO2006097537 | A2 * | 9/2009 | C07K 14/605 |
| WO | 10015664 | A1 | 2/2010 | |
| WO | 11039367 | A2 | 4/2011 | |
| WO | 11064352 | A1 | 6/2011 | |
| WO | 2011138421 | A1 | 11/2011 | |
| WO | 11161161 | A1 | 12/2011 | |
| WO | 12065993 | A1 | 5/2012 | |
| WO | WO2012/080471 | A1 * | 6/2012 | A61K 9/20 |
| WO | 2012107476 | A1 | 8/2012 | |
| WO | 2013/037690 | A1 | 3/2013 | |
| WO | 13098372 | A1 | 7/2013 | |
| WO | 13171166 | A1 | 11/2013 | |
| WO | 13171167 | A1 | 11/2013 | |
| WO | 13174768 | A1 | 11/2013 | |
| WO | 2014066992 | A1 | 5/2014 | |
| WO | 14124860 | A1 | 8/2014 | |
| WO | 14140284 | A1 | 9/2014 | |
| WO | 2015071355 | A1 | 5/2015 | |
| WO | 15085044 | A1 | 6/2015 | |
| WO | 2016164413 | A1 | 10/2016 | |
| WO | 2017186896 | A1 | 11/2017 | |

OTHER PUBLICATIONS

Howard LeWine. Diabetes can strike—hard—even when weight is normal. https://www.health.harvard.edu/blog/diabetes-can-strike-hard-even-when-weight-isnormal-201208085121 (Year: 2012).*
Capitza et al. Semaglutide, a Once-Weekly Human GLP-1 Analog, Does Not Reduce the Bioavailability of the Combined Oral Contraceptive, Ethinylestradiol/Levonorgestrel. J Clin Pharmacol. May 2015; 55(5): 497-504. Published online Jan. 14, 2015. (Year: 2015).*
Novo Nordisk-a focused healthcare company; LEADER hedline results; Mar. 4, 2016.
Andre J Scheen "Cardiovascular safety of albiglutide and other glucagon-like peptide-1 receptor agonists" The Lancet Diabetes and Endocrinology 2015 vol. 3 No. 9 pp. 667-669.
Anonymous: "Novo Nordisk successfully completes first phase 3a trial with semaglutide in people with type 2 diabetes," Novo Nordisk A/S Company Announcement No. 41/2015, Jun. 10, 2015, Retrieved from the Internet: URL: https://www.novonordisk.com/bin/getPDF.1934243.pdf, [retrieved on May 30, 2017], pp. 1-3.
Asfandyar Sheikh, "Direct Cardiovascular Effects of Glucagon Like Peptide-1" Diabetology & Metabolic Syndrome 2013 vol. 5 No. 1 p. 47; 13 pages.
Cordiner, R et al., "SUSTAIN-6: cardiovascular safety of a once-weekly GLP-1 receptor agonist", Practical Diabetes, 2016, vol. 33, No. 8, pp. 266-268a.
Marso, S. P. et al., "Semaglutide and cardiovascular outcomes in patients with Type 2 Diabetes", The New England Journal of Medicine, 2016, vol. 375, pp. 1834-1844.

(Continued)

*Primary Examiner* — Li N Komatsu
*Assistant Examiner* — Jia-Hai Lee
(74) *Attorney, Agent, or Firm* — Foley & Lardner LLP

(57) ABSTRACT

The present invention relates to the GLP-1 receptor agonist semaglutide for use in medicine.

13 Claims, 2 Drawing Sheets

(56) References Cited

OTHER PUBLICATIONS

S Halimi "Securite cardiovasculaire des incretines et des inhibiteurs des co-transporteurs sodium-glucose de type 2 (SGLT2). Revue" Medecine Des Maladies Metaboliques 2015 vol. 9 No. 8 pp. 768-775.
Novo Nordisk Company Announcement, "Victoza significantly reduces the risk of major adverse cardiovascular events in the LEADER trial," Bagsvaerd, Denmark, Mar. 4, 2016.
Cardioangiology, 2012, vol. 71 No. 5, pp. 470-476.
Diabetes, 2012, vol. 55, No. Supplement 1, p. S-135 (I-P-177).
Japanese Journal of Clinical Medicine, 2011, vol. 69 No. 5, pp. 836-841.
Damian Garde, "Novo Nordisk successfully completes first phase 3a trial with semaglutide in people with type 2 diabetes", Fierce Biotech, Jul. 10, 2015, https://www.fiercebiotech.com/biotech/novo-nordisksuccessfully-completes-first-phase-3a-trial-semaglutide-people-type-2-diabetes., accessed Jun. 18, 2021.
Hess et al. "Cardiovascular disease and diabetes: the vulnerable patient," European Heart Journal Supplements, Nov. 2012, vol. 14, Suppl_B,, pp. B4-B13.
Nauck et al., "A Phase 2, Randomized, Dose-Finding Study of the Novel Once-Weekly Human GLP-1 Analog, Semaglutide, Compared With Placebo and Open-Label Liraglutide in Patients With Type 2 Diabetes," Diabetes Care, Feb. 2016, vol. 39, pp. 231-241.
U.S. Dept. of HHS Food and Drug Administration, "Guidance for Industry, Diabetes Mellitus—Evaluating Cardiovascular Risk in New Antidiabetic Therapies to Treat Type 2 Diabetes", CDER, Dec. 2008, pp. 1-5.
Monami et al., "Glucagon-Like Peptide-1 Receptor Agonists and Cardiovascular Events: A Meta-Analysis of Randomized Clinical Trials", Experimental Diabetes Research, Apr. 2011, vol. 2011, Article 215764, pp. 1-10.
Scheen, "Cardiovascular safety of albiglutide and other glucagon-like peptide-1 receptor agonists," The Lancet, Aug. 12, 2015, vol. 3, p. 667-669.
*OSI Pharmaceuticals* v. *Apotex Inc*., 2018-1925 (Fed. Cir. 2019).
Holman et al., "Effects of Once-Weekly Exenatide on Cardiovascular Outcomes in Type 2 Diabetes," The New England Journal of Medicine, Sep. 14, 2017, vol. 377, No. 13, pp. 1228-1239.
Pfeffer et al., "Lixisenatide in Patients with Type 2 Diabetes and Acute Coronary Syndrome", The New England Journal of Medicine, Dec. 3, 2015, vol. 373, No. 23, pp. 2247-2257.
Fisher, "Glucagon-like peptide 1 receptor agonists and cardiovascular risk in type 2 diabetes: a clinical perspective," Diabetes, Obesity & Metabolism, Aug. 2014, vol. 17, No. 4, pp. 335-342.
Ferrannini et al., "Impact of glucose-lowering drugs on cardiovascular disease in type 2 diabetes", Eur Heart J, Jun. 2015, vol. 36, No. 34, pp. 2288-2296.
Wang et al., "Blood pressure-lowering effects of GLP-1 receptor agonists exenatide and liraglutide: a meta-analysis of clinical trials", Diabetes Obes Metab., Feb. 2013, vol. 15, No. 8, pp. 737-749.
Van Genugten et al., "Extra-pancreatic effects of incretin-based therapies: Potential benefit for cardiovascular-risk management in type 2 diabetes", Diabetes Obesity and Metabolism, Dec. 2012, vol. 15, No. 7, pp. 593-606.
Anagnostis et al., "Glucagon-like peptide-1-based therapies and cardiovascular disease: looking beyond glycaemic control," Diabetes, Obesity and Metabolism, Apr. 2011, vol. 13, No. 4, pp. 302-312.
Monami et al., Effects of glucagon-like peptide-1 receptor agonists on cardiovascular risk: a meta-analysis of randomized clinical trials, Diabetes, Obesity and Metabolism, 2014, vol. 16, pp. 38-47.
Mundil Dhanwantee et al "GLP-1 receptor agonists: a clinical perspective on cardiovascular effects" Diabetes & Vascular Disease Research, 2012, vol. 9, No. 2 pp. 95-108.
Sivertsen et al., "The effect of glucagon-like peptide 1 on cardiovascular risk", Nat. Rev. Cardiol., Jan. 31, 2012, vol. 9, No. 4, pp. 209-222.
Gejl et al., Risk of cardiovascular disease: The effects of diabetes and anti-diabetic drugs—A nested case-control study, International Journal of Cardiology, 2015, vol. 178, pp. 292-296.
Caterson I. D., "Abstract 12630: Cardiovascular Safety of Liraglutide: Pooled Analysis of Major Adverse Cardiovascular Events across Weight Management and Type 2 Diabetes Development Programs", Nov. 2015, Circulation. vol. 132, 3 pages.
Marso et al., "Supplementary Appendix—Semaglutide and cardiovascular outcomes in patients with type 2 diabetes", NEJM, 2016, vol. 375, pp. 1-109.
Novo Nordisk press release, Sep. 16, 2016.
Nainggolan, "Now Novo Says Semaglutide Cuts CV Risk: SUSTAIN-6 Top-line Data", Medscape, Apr. 29, 2016, 2 pages.
Nainggolan, "Now Novo Says Semaglutide Cuts CV Risk: SUSTAIN-6 Top-line Data", Medscape, Apr. 2016, retrieved May 2, 2016 at www.medscape.com/viewarticle/862644.
Novo Nordisk press release, Jul. 10, 2015, 3 pages.
Scheel-Thomsen et al "Diabetes and Stroke: Liraglutide is associated with a decrease risk of stroke in type 2 diabetes mellitus. A Nested case-control study" European Journal of Nuerology 2014 vol. 21 No. Suppl 1 p. 154.
Ozempic Assessment Report, EMA, published on Dec. 14, 2017, pp. 1-156.
NCT01720446, "Trial to Evaluate Cardiovascular and Other Long-term Outcomes With Semaglutide in Subjects With Type 2 Diabetes (SUSTAIN™ 6)", ClinicalTrials.gov, May 28, 2015, version 24, pp. 1-14.
European Medicines Agency, "Guideline on clinical investigation of medicinal products in the treatment or prevention of diabetes mellitus", May 14, 2012, pp. 1-28.
Menon et al., "Cardiovascular Safety Evaluation in the Development of New Drugs for Diabetes Mellitus", Circulation, Jun. 2014, vol. 129, pp. 2705-2713.
Tibble et al., "Longer acting GLP-1 receptor agonists and the potential for improved cardiovascular outcomes: a review of current literature", Expert Reviews of Endocrinology & Metabolism, 2013, vol. 8, No. 3, pp. 247-259.
Lorenz et al., "Recent progress and future options in the development of GLP-1 receptor agonists for the treatment of diabesity", Bioorganic & Medicinal Chemistry Letters, May 2013, vol. 23, pp. 4011-4018.
Courreges et al., "Beneficial effects of once-daily liraglutide, a human glucagon-like peptide-1 analogue, on cardiovascular risk biomarkers in patients with Type 2 diabetes", Diabetic Medicine, 2008, vol. 25, pp. 1129-1131.
Varanasi et al., "Clinical use of liraglutide in type 2 diabetes and its effects on cardiovascular risk factors", Endocrine Practice, Mar./Apr. 2012, vol. 18, No. 2, pp. 140-145.
Turnbull et al., "Intensive glucose control and macrovascular outcomes in type 2 diabetes", Diabetologia, Jun. 2009, vol. 52, pp. 2288-2298.
Stamler et al., "Diabetes, other risk factors, and 12-yr cardiovascular mortality for men screened in the Multiple Risk Factor Intervention Trial", Diabetes Care, Feb. 1993, vol. 16, No. 2, pp. 434-444.
Huxley et al., "Excess risk of fatal coronary heart disease associated with diabetes in men and women: meta-analysis of 37 prospective cohort studies", BMJ, Dec. 2006, vol. 332, pp. 1-6.
Leon et al., "Diabetes and cardiovascular disease: Epidemiology, biological mechanisms, treatment recommendations and future research", World J Diabetes, Oct. 10, 2015, vol. 6, No. 13, pp. 1246-1258.
The Emerging Risk Factors Collaboration, "Diabetes mellitus, fasting blood glucose concentration, and risk of vascular disease: a collaborative meta-analysis of 102 prospective studies", Lancet, Jun. 26, 2010, vol. 375, pp. 2215-2222.
Haffner et al., "Mortality From Coronary Heart Disease in Subjects With Type 2 Diabetes and in Nondiabetic Subjects With and Without Prior Myocardial Infarction", The New England Journal of Medicine, Jul. 23, 1998, vol. 339, No. 4, pp. 229-234.
"Phenol", DrugBank, Jun. 13, 2005, retrieved May 5, 2023 at: https://go.drugbank.com/drugs/DB03255.

(56) References Cited

OTHER PUBLICATIONS

Zhang et al., "Glycosylated Hemoglobin in Relationship to Cardiovascular Outcomes and Death in Patients with Type 2 Diabetes: A Systematic Review and Meta-Analysis", PLoS One, Aug. 9, 2012, vol. 7, No. 8, e42551, pp. 1-11.
Petrie "The cardiovascular safety of incretin-based therapies: a review of the evidence" Cardiovascular Diabetology, 2013, vol. 12, No. 130, pp. 1-12.
Novo Nordisk, "A Long-term, Randomised, Double-blind, Placebo-controlled, Multinational, Multi-centre Trial to Evaluate Cardiovascular and Other Long-term Outcomes With Semaglutide in Subjects With Type 2 Diabetes (SUSTAIN™ 6—Long-term Outcomes)", NCT clinical trials database, NCT 01720446, Jan. 25, 2016, available from: https://clinicaltrials.gov/ct2/history/NCT01720446?V_25=View#StudyPageTop.
Case No. T0326/15-3.3.07, Decision of Technical Board of Appeal 3.3.07 of Nov. 21, 2017.
Holman et al., "Cardiovascular outcome trials of glucose-lowering drugs or strategies in type 2 diabetes", The Lancet, Jun. 2014, vol. 383, pp. 2008-2017.
Novo Nordisk "Efficacy and Safety of Semaglutide Once-weekly Versus Placebo in Drug-naive Subjects With Type 2 Diabetes (SUSTAIN-1)" NCT clinical trials database, NCT02054897, Mar. 17, 2016, available from https://clinicaltrials.gov/ct2/history/NCT02054897?V _ 16=View#StudyPage Top.
Lau et al., "Discovery of the Once-Weekly Glucagon-Like Peptide-1 (GLP-1) Analogue Semaglutide", J. Med Chem, Aug. 2015, vol. 58, No. 18, pp. 7370-7380.
European Patent Application No. 16167458, filed Apr. 28, 2016, 33 pages.
European Patent Application No. 16188262, filed Sep. 12, 2016, 34 pages.
"Oral semaglutide showing promise as type 2 diabetes treatment", Diabetes, Apr. 5, 2016, retrieved from https://www.diabetes.co.uk/news/2016/apr/oral-semaglutide-showing[1]promise-as-type-2-diabetes-treatment-95318018.html.
Applicant's submission of Jun. 17, 2019 during examination of the European Patent Application No. 17721109.1.
"Semaglutide significantly reduces the risk of major adverse cardiovascular events in the SUSTAIN 6 trial", Valuefokus.de, Apr. 28, 2016, retrieved from https://www.valuefokus.de/betriebsnachrichten/presse/1810285-semaglutide[1]significantly-reduces-the-risk-of-major-adverse-cardiovascular-events-in-the-sustain-6-trial.
"Trial to Evaluate Cardiovascular and Other Long-term Outcomes With Semaglutide in Subjects With Type 2 Diabetes (SUSTAIN™ 6)", ClinicalTrials.gov, NCT01720446, Apr. 4, 2016, v26, retrieved from https://clinicaltrials.gov/ct2/history/NCT01720446?V_26=View#StudyPageTop.
Kalra et al., "Glucagon-like peptide-1 receptor agonists in the treatment of type 2 diabetes: Past, present, and future", Indian Journal of Endocrinology and Metabolism, Mar. 2016, vol. 20, pp. 254-267.
Lorber, "GLP-1 Receptor Agonists: Effects on Cardiovascular Risk Reduction", Cardiovascular Therapeutics, 2013, vol. 31, pp. 238-249.
Deacon et al., "Dipeptidyl peptidase IV resistant analogues of glucagon-like pep[1]tide-1 which have extended metabolic stability and improved biological activity", Diabetologica, Feb. 1998, vol. 41, pp. 271-278.
FDA, Full Prescribing Information product Victoza, published 2010.
Marso et al., "Design of the liraglutide effect and action in diabetes: Evaluation of cardiovascular outcome results (LEADER) trial", Am Heart J, Nov. 2013, vol. 166, pp. 823-830.
Cho, "Cardiovascular effects of the incretin-based therapy: the good, the bad, or the ugly?", J. Diabetes Investig., Nov. 2015, vol. 6, pp. 597-599.
Company Announcement, Novo Nordisk A/S, No. 31/2016, "Semaglutide significantly reduces the risk of major adverse cardiovascular events in the SUSTAIN 6 trial", Apr. 28, 2016.
NCT01324505, "Effect of Oral Contraceptives After Administration of Semaglutide in Subjects With Type 2 Diabetes", ClinicalTrials.gov, retrieved from https://classic.clinicaltrials.gov/ct2/show/NCT01324505.
Lovshin et al., "Incretin-based therapies for type 2 diabetes mellitus", Nature Reviews Endocrinology, May 2009, vol. 5, pp. 262-269.
Matheus et al., "Impact of diabetes on cardiovascular disease: an update", Int. J. Hypertens., Mar. 2013, vol. 2013, pp. 1-16.
European Patent Office, Opposition Division; Providing Letter from Opponent 03; European Patent Application No. 17721109.1; Nov. 20, 2024; 4 pages.
Novo Nordisk; "A Long-term, Randomised, Double-blind, Placebo-controlled, Multinational, Multi-centre Trial to Evaluate Cardiovascular and Other Long-term Outcomes With Semaglutide in Subjects With Type 2 Diabetes (SUSTAIN 6—Long-term Outcomes)"; NCT clinical trials database, NCT 01720446, Version 19, Dec. 5, 2013, available from https://clinicaltrials.gov/study/NCT01720446?term=NCT01720446&rank=1&a=19&tab=history#version-content-panel; 1 page.
Novo Nordisk; "A Long-term, Randomised, Double-blind, Placebo-controlled, Multinational, Multi-centre Trial to Evaluate Cardiovascular and Other Long-term Outcomes With Semaglutide in Subjects With Type 2 Diabetes (SUSTAIN 6—Long-term Outcomes)"; NCT clinical trials database, NCT 01720446, Version 20, Dec. 11, 2013, available from https://clinicaltrials.gov/study/NCT01720446?term=NCT01720446&rank=1&a=20&tab=history#version-content-panel; 1 page.
Public Law 110-85, 110th Congress "Food and Drug Administration Amendments Act of 2007"; Sep. 27, 2007; pp. 823 (front page), 916, and 917.; available from https://www.govinfo.gov/content/pkg/PLAW-110publ85/pdf/PLAW-110publ85.pdf#page=82.
Company Announcement, "Novo Nordisk successfully completes fifth phase 3a trial with semaglutide in people with type 2 diabetes" (Feb. 23, 2016).
Novo Nordisk, Annual Report 2015.
Marso et al., Cardiovascular safety of liraglutide in a patient-level pooled analysis of phase 2-3 liraglutide clinical development studies, Diabetes & Vascular Disease Research, 2011, vol. 8, No. 3, pp. 237-240.
Decision of Case No. T 0326/15, Nov. 21, 2017, 12 pages.
Decision of Case No. T0423/09, Feb. 3, 2011, 16 pages.
White et al., "Alogliptin after Acute Coronary Syndrome in Patients with Type 2 Diabetes" N Engl J Med, Oct. 2013, vol. 369, No. 14, pp. 1327-1335.
Zinman et al., "Empagliflozin, Cardiovascular Outcomes, and Mortality in Type 2 Diabetes", N Engl J Med, Nov. 2015, vol. 373, No. 22, pp. 2117-2127.
EMA Guidance "Points to consider on switching between superiority and noninferiority" EMA, Jul. 27, 2000, London, CPMP/EWP/482/99, pp. 1-11.
Schumi et al., "Through the looking glass: understanding non-inferiority", Trials, 2011, vol. 12, No. 106, pp. 1-12.
U.S. Label Ozempic®, Sep. 2023.
Madsbad, S. et al.; "An overview of once-weekly glucagon-like peptide-1 receptor agonists—available efficacy and safety data and perspectives for the future"; Diabetes, Obesity and Metabolism, vol. 13, No. 5; May 2011; pp. 394-407.
Meier, Juris J.; "GLP-1 receptor agonists for individualized treatment of type 2 diabetes mellitus"; Nat. Rev. Endocrinol., vol. 8, No. 12; Sep. 4, 2012; pp. 728-742.
Perk, Joep et al.; "European Guidelines on cardiovascular disease prevention in clinical practice (version 2012)"; European Heart Journal, vol. 33; May 3, 2012; pp. 1635-1701.
Bacharova et al., "The Role of ECG in the Diagnosis of Left Ventricular Hypertrophy," Current Cardiology Reviews, May 2014; 10: 257-261.
Eng, John et al.; "Isolation and Characterization of Exendin-4, an Exendin-3 Analogue, from Heloderma suspectum Venom"; The Journal of Biological Chemistry, vol. 267, No. 11; Apr. 15, 1992; pp. 7402-7405.

(56) References Cited

OTHER PUBLICATIONS

European Medicines Agency, Committee for Medicinal Products for Human Use (CHMP), Saxenda (Liraglutide) Assessment Report, EMA/143005/2015, Feb. 11, 2015; 91 pages.
Hirshberg, Boaz et al.; "Cardiovascular Outcome Studies With Novel Antidiabetes Agents: Scientific and Operational Considerations"; Diabetes Care, vol. 36, Suppl. 2; Aug. 2013; pp. S253-S258.
Husain, Mansoor et al.; "Semaglutide (SUSTAIN and PIONEER) reduces cardiovascular events in type 2 diabetes across varying cardiovascular risk"; Diabetes Obes Metab., vol. 22; Feb. 5, 2020; pp. 442-451.
Kocabas, H. et al.; "Comparison of phenol and alcohol neurolysis of tibial nerve motor branches to the gastrocnemius muscle for treatment of spastic foot after stroke: a randomized controlled pilot study"; Eur. J. Phys. Rehabil Med., vol. 46, No. 1; Feb. 5, 2010; pp. 5-10.
Martin-Timon et al., "Type 2 diabetes and cardiovascular disease: Have all risk factors the same strength?" World J Diabetes Aug. 1, 20145; 5(4): 444-470.
National Library of Medicine, National Center for Biotechnology Information; ClinicalTrials.gov Id NCT05429593; Sponsor Novo Nordisk A/S; "A Research Study Investigating How Semaglutide and Dapagliflozin Act in Your Body When Dosed in One Tablet"; Aug. 7, 2024; 13 pages.
National Library of Medicine; National Center for Biotechnology Information; NCT01720446; ClinicalTrials.gov; Oct. 14, 2014; 32 pages.
Novo Nordisk A/S; Ozempic Semaglutide Injection 0.5 mg, 1mg, 2mg; Prescribing Information; Sep. 2023 (revised Jan. 2025); 16 pages.
Page, Michael R.; "Gila Monster Venom, Gut Hormones, and Diabetes: The Winding Path to Drug Discovery"; Pharmacy Times, Sep. 9, 2014; 7 pages.
Weber, Patricia; "Nutritional Challenges of a Dual Diagnosis: Chronic Kidney Disease and Diabetes"; Diabetes Spectrum, vol. 21, No. 1; Jan. 2008; pp. 26-29.
Prasad-Reddy, Lalita et al.; "A clinical review of GLP-1 receptor agonists: efficacy and safety in diabetes and beyond"; Drugs in Context; Jul. 9, 2015; 19 pages.
Romero et al., "The Modification of Diet in Renal Disease 4-calculated glomerular filtration rate is a better prognostic factor of cardiovascular events than classical cardiovascular risk factors in patients with peripheral arterial disease," J Vasc Surg .; vol. 56, No. 5; Nov. 2012; pp. 1324-1330.
Saraiva, Francisco Kerr et al.; "Cardiovascular effects of Glucagon-like peptide 1 (GLP-1) receptor agonists"; Cardiovasc Diabetol., vol. 13, No. 142; Oct. 22, 2014; 11 pages.
Thomas et al., "Chronic Kidney Disease and Its Complications," Prim Care. Jun. 2008 ; 35(2): 329.
U.S. Patent and Trademark Office; Non-Final Office Action; U.S. Appl. No. 19/197,677; Aug. 14, 2025; 31 pages.
Vilsboll, Tina; "Liraglutide: a human GLP-1 analog for Type 2 diabetes"; Therapy, vol. 6, No. 2; Jan. 2009; pp. 199-207.

* cited by examiner

SEMAGLUTIDE IN CARDIOVASCULAR CONDITIONS

CROSS-REFERENCE TO RELATED APPLICATIONS

This application is a 35 U.S.C. § 371 National Stage application of International Application PCT/EP2017/060160 (WO 2017/186896), filed Apr. 28, 2017, which claims priority to European Patent Applications 16167458.5, filed Apr. 28, 2016 and 16188262.6, filed Sep. 12, 2016; the contents of which are incorporated herein by reference.

The present invention relates to the GLP-1 receptor agonist semaglutide for use in treating a subject having diabetes and high cardiovascular risk.

BACKGROUND

Diabetes is a metabolic disorder characterized by hyperglycaemia that is associated with a high risk of cardiovascular and other serious health-related consequences. A person with diabetes is two to three times more likely to die from cardiovascular causes than people with no history of diabetes, even after controlling for other cardiovascular risk factors. They are also at very high risk of developing serious microvascular complications ultimately leading to premature death: nephropathy and renal failure, retinal disease and blindness, autonomic and peripheral neuropathy, as well as other conditions related to the cardiovascular system: hypertension, lower limb amputation, cognitive decline, and erectile dysfunction.

The majority of people with diabetes have type 2 diabetes, which is characterised by insulin resistance and eventually impaired insulin secretion. Optimal glycaemic control is the treatment goal in subjects with type 2 diabetes, since the risk of long-term complications is increased with poor glycaemic control. Despite the availability of several oral anti-diabetic drugs and insulin, a significant proportion of subjects with type 2 diabetes do not achieve the recommended target levels for glycaemic control and are at high risk of developing cardiovascular disease or microvascular complications. Thus, there is an unmet medical need for treatment alternatives that not only provide glycaemic control but also reduce the risk of cardiovascular disease in subjects with type 2 diabetes.

SUMMARY

In some embodiments the present invention relates to a method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method delays or reduces development of a major adverse cardiovascular event (MACE).

BRIEF DESCRIPTION OF DRAWINGS

FIG. 1-2 show the number of subjects at risk for the relevant event(s) at different time points after randomisation and are Kaplan-Meier plots of time to event.

DESCRIPTION

Figure 1:
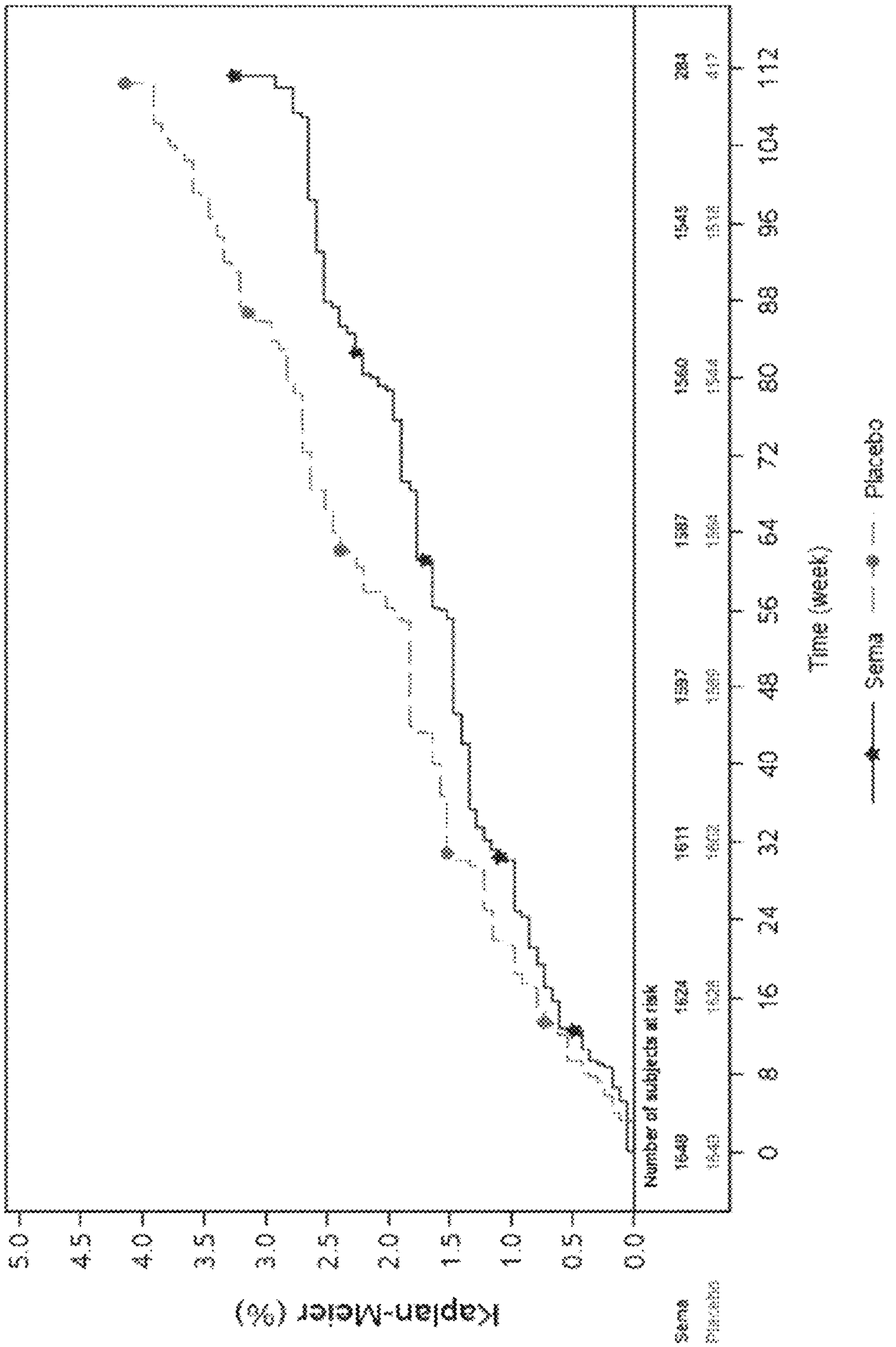
FIG. 1 shows time from randomisation to first non-fatal MI following administration of semaglutide (Sema) or its placebo.

The present invention relates to methods of administering the GLP-1 receptor agonist semaglutide to a subject having diabetes and high cardiovascular risk. The term "high cardiovascular risk" as used herein refers to clinical evidence of at least one cardiovascular disease and/or subclinical evidence of at least one cardiovascular disease. In some embodiments high cardiovascular risk is present if the subject has clinical or subclinical evidence of at least one cardiovascular disease.

In some embodiments the present invention relates to a method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method reduces the risk of cardiovascular events compared to placebo. In some embodiments the clinical evidence of cardiovascular disease and/or subclinical evidence of cardiovascular disease were present before initiation of semaglutide administration.

In some embodiments the present invention relates to a method of reducing the risk of MACE in subjects with type 2 diabetes mellitus and high cardiovascular risk. In some embodiments the present invention relates to a method of reducing the risk of MACE in subjects with type 2 diabetes mellitus and high cardiovascular risk, wherein said MACE is selected from the group consisting of non-fatal MI, non-fatal stroke, CV death caused by MI, and CV death caused by stroke. In some embodiments said MACE is selected from the group consisting of non-fatal MI and CV death caused by MI. In some embodiments said MACE is selected from the group consisting of non-fatal stroke and CV death caused by stroke.

In some embodiments the present invention relates to a method of delaying myocardial infarction or stroke in subjects with type 2 diabetes mellitus and high cardiovascular risk. In some embodiments the terms "delaying" as used herein refers to "preventing". In some embodiments the present invention relates to a method of preventing cardiovascular events in subjects with type 2 diabetes, wherein said "cardiovascular events" is one or more major adverse cardiovascular events, and wherein "major adverse cardiovascular event" is as defined herein.

In some embodiments the present invention relates to a method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method reduces or delays a major adverse cardiovascular event (MACE).

In some embodiments MACE is events selected from the group consisting of cardiovascular (CV) death, non-fatal MI, non-fatal stroke, revascularisation, hospitalisation for unstable angina pectoris, and hospitalisation for heart failure. The term "non-fatal MI" as used herein refers to non-fatal myocardial infarction. In some embodiments MACE is events selected from the group consisting of CV death, non-fatal MI, and non-fatal stroke.

In some embodiments the method reduces or delays a major adverse cardiovascular event (MACE). In some embodiments the method reduces the risk of said subject developing a major adverse cardiovascular event (MACE). In some embodiments the method reduces the risk of said subject developing its first MACE. Thus, in some embodiments the MACE referred to herein is first MACE, e.g. after initiating administration of semaglutide. The term "first MACE" as used herein refers to the first MACE event of a subject after initiation of semaglutide administration.

In some embodiments MACE is selected from the group consisting of CV death, non-fatal MI, non-fatal stroke, revascularisation, hospitalisation for heart failure, and hospitalisation for unstable angina pectoris. In some embodiments MACE (e.g. selected from the group consisting of CV death, non-fatal MI, non-fatal stroke, revascularisation, hospitalisation for heart failure, and hospitalisation for unstable angina pectoris) is reduced or delayed by at least 1% compared to placebo. In some embodiments MACE (e.g. selected from the group consisting of CV death, non-fatal MI, non-fatal stroke, revascularisation, hospitalisation for heart failure, and hospitalisation for unstable angina pectoris) is reduced or delayed by from about 20% to about 35% compared to placebo. In some embodiments MACE (e.g. selected from the group consisting of CV death, non-fatal MI, non-fatal stroke, revascularisation, hospitalisation for heart failure, and hospitalisation for unstable angina pectoris) is reduced about 27% compared to placebo. In some embodiments the first MACE (e.g. selected from the group consisting of CV death, non-fatal MI, non-fatal stroke, revascularisation, hospitalisation for heart failure, and hospitalisation for unstable angina pectoris) is reduced or delayed by at least 1% compared to placebo. In some embodiments the first MACE (e.g. selected from the group consisting of CV death, non-fatal MI, non-fatal stroke, revascularisation, hospitalisation for heart failure, and hospitalisation for unstable angina pectoris) is reduced or delayed by from about 20% to about 27% compared to placebo. In some embodiments the first MACE (e.g. selected from the group consisting of CV death, non-fatal MI, non-fatal stroke, revascularisation, hospitalisation for heart failure, and hospitalisation for unstable angina pectoris) is reduced about 27% compared to placebo.

In some embodiments MACE is selected from the group consisting of CV death, non-fatal MI, and non-fatal stroke. In some embodiments MACE (e.g. selected from the group consisting of CV death, non-fatal MI, and non-fatal stroke) is reduced or delayed by at least 10% compared to placebo. In some embodiments MACE (e.g. selected from the group consisting of CV death, non-fatal MI, and non-fatal stroke) is reduced or delayed by from about 20% to about 30% compared to placebo. In some embodiments MACE (e.g. selected from the group consisting of CV death, non-fatal MI, and non-fatal stroke) is reduced or delayed about 26% compared to placebo. In some embodiments MACE (e.g. selected from the group consisting of CV death, non-fatal MI, and non-fatal stroke) has a hazard ratio of about 0.74 compared to placebo. In some embodiments MACE (e.g. selected from the group consisting of CV death, non-fatal MI, and non-fatal stroke) has a hazard ratio of 0.74 with a 95% CI of (0.58; 0.95) compared to placebo. In some embodiments the risk of said subject developing a MACE (e.g. selected from the group consisting of CV death, non-fatal MI, and non-fatal stroke) is reduced by at least 10% compared to placebo. In some embodiments the subject developing its first MACE (e.g. selected from the group consisting of CV death, non-fatal MI, and non-fatal stroke) is reduced or delayed by at least 10% compared to placebo. In some embodiments the first MACE (e.g. selected from the group consisting of CV death, non-fatal MI, and non-fatal stroke) is reduced or delayed by from about 20% to about 30% compared to placebo. In some embodiments the first MACE (e.g. selected from the group consisting of CV death, non-fatal MI, and non-fatal stroke) is reduced or delayed about 26% compared to placebo. In some embodiments the subject developing its first MACE (e.g. selected from the group consisting of CV death, non-fatal MI, and non-fatal stroke) has a hazard ratio of about 0.74 compared to placebo. In some embodiments the subject developing its first MACE (e.g. selected from the group consisting of CV death, non-fatal MI, and non-fatal stroke) has a hazard ratio of 0.74 with a 95% CI of (0.58; 0.95) compared to placebo.

In some embodiments the MACE is non-fatal MI. In some embodiments the non-fatal MI is reduced or delayed by at least 10% compared to placebo. In some embodiments the non-fatal MI is reduced or delayed by from about 15% to about 35% compared to placebo. In some embodiments the non-fatal MI is reduced or delayed by about 26% compared to placebo.

In some embodiments the MACE is non-fatal stroke. In some embodiments the non-fatal stroke is reduced or delayed by at least 10% compared to placebo. In some embodiments the non-fatal stroke is reduced or delayed by from about 20% to about 60% compared to placebo. In some embodiments the non-fatal stroke is reduced or delayed by from about 30% to about 50% compared to placebo. In some embodiments the non-fatal stroke is reduced or delayed by about 39% compared to placebo.

In some embodiments the MACE is revascularisation. In some embodiments the revascularisation is reduced or delayed by at least 10% compared to placebo. In some embodiments the revascularisation is reduced or delayed by from about 20% to about 60% compared to placebo. In some embodiments the revascularisation is reduced or delayed by from about 30% to about 50% compared to placebo. In some embodiments the revascularisation is reduced or delayed by about 38% compared to placebo. Revascularisation may be coronary revascularisation or peripheral revascularisation.

In some embodiments the MACE is hospitalisation for unstable angina pectoris. In some embodiments the hospitalisation for unstable angina pectoris is reduced or delayed by at least 10% compared to placebo. In some embodiments the hospitalisation for unstable angina pectoris is reduced or delayed by from about 10% to about 30% compared to placebo. In some embodiments the hospitalisation for unstable angina pectoris is reduced or delayed by about 18% compared to placebo.

In some embodiments the administration of semaglutide is a chronic treatment in which semaglutide is administered for at least 16 months (such as at least 30 months, and optionally up to 54 months), and wherein said method reduces or delays non-fatal myocardial infarction (MI).

In some embodiments the administration of semaglutide is a chronic treatment in which semaglutide is administered for at least 18 months (such as at least 30 months, and optionally up to 54 months), and wherein said method reduces the need or risk of requiring revascularisation.

In some embodiments the MACE is CV death. In some embodiments the CV death is reduced by at least 1% compared to placebo. In some embodiments the CV death is reduced or delayed by from about 1% to about 3% compared to placebo. In some embodiments the CV death is reduced or delayed by about 2% compared to placebo.

The term "placebo" as used herein refers to a formulation identical to the semaglutide formulation except not comprising semaglutide and the placebo was administered in the volume used in the equivalent semaglutide dosage. A subject receiving placebo may also include concomitant medication, such as one or more oral anti-diabetic drugs (OADs), or human NPH insulin or long-acting insulin analogue or premixed insulin, alone or in combination with one or two OAD(s).

"CV death" may be defined as death, wherein the cause of death is selected from the group consisting of cardiovascular disease or is unknown. In some embodiments CV death may be defined as death where no clearly documented non-cardiovascular cause exists. CV death may include death resulting from an acute myocardial infarction, sudden cardiac death, death due to heart failure, death due to stroke, death due to cardiovascular procedures, death due to CV haemorrhage, and death due to other CV causes with a specific, known CV cause (e.g., pulmonary embolism or peripheral arterial disease).

"Non-fatal MI" may be defined as myocardial necrosis consistent with myocardial ischemia without death of the subject. In some embodiments MI is diagnosed based on the redefinitions suggested by the ESC (European Society of Cardiology)/ACCF (American College of Cardiology Foundation)/AHA (American Heart Association)/WHF (World Heart Federation) task force, as described in Thygesen K, et al. "Universal Definition of Myocardial Infarction." J Am Coll Cardiol 2007 Nov. 27; 50 (22): 2173-95.

"Revascularisation" may be defined as restoration of perfusion to a body part or organ that has suffered ischemia, e.g. by unblocking obstructed or disrupted blood vessels or by surgically implanting replacements such as a stent. More specifically, "coronary revascularisation" may be defined as improvement of myocardial blood flow, and "peripheral revascularisation" may be defined as improvement of peripheral arterial blood flow.

"Hospitalisation for unstable angina pectoris" may be defined as unscheduled hospitalisation characterised by 1) ischemic discomfort 10 minutes in duration occurring at rest, or in an accelerating pattern with frequent episodes associated with progressively decreased exercise capacity; 2) no elevation in cardiac biomarkers and no evidence of acute MI; and 3) at least one selected from the group consisting of: a. New or worsening ST or T wave changes on resting ECG (in the absence of confounders, such as LBBB or LVH) Transient ST elevation (duration<20 minutes), and/or new ST elevation at the 3 point in two contiguous leads with the cut-points: ≥0.1 mV in all leads other than leads V2-V3 where the following cut-points apply: ≥0.2 mV in men 40 years (≥0.25 mV in men <40 years) or ≥0.15 mV in women, and/or ST depression and T-wave changes, and/or New horizontal or down-sloping ST depression≥0.05 mV in two contiguous leads and/or new T inversion≥0.3 mV in two contiguous leads with prominent R wave or R/S ratio >1; b. Definite evidence of inducible myocardial ischemia as demonstrated by: an early positive exercise stress test, defined as ST elevation or 2 mm ST depression prior to 5 mets, or stress echocardiography (reversible wall motion abnormality), or myocardial scintigraphy (reversible perfusion defect), or MRI (myocardial perfusion deficit under pharmacologic stress), and believed to be responsible for the myocardial ischemic symptoms/signs; c. Angiographic evidence of new or worse 70% lesion and/or thrombus in an epicardial coronary artery that is believed to be responsible for the myocardial ischemic symptoms/signs; and d. Need for coronary revascularization procedure (PCI or CABG) for the presumed culprit lesion(s) (this criterion would be fulfilled if revascularization was undertaken during the unscheduled hospitalization, or subsequent to transfer to another institution without interceding home discharge). The term "cardiac biomarkers" in connection with unstable angina pectoris may include troponin and CK-MB.

"Non-fatal stroke" may be defined as an acute episode of focal or global neurological dysfunction caused by brain, spinal cord, or retinal vascular injury as a result of haemorrhage or infarction, e.g., ischemic stroke, or haemorrhagic stroke, without death of the subject. In some embodiments ischemic stroke is defined as an acute episode of focal cerebral, spinal, or retinal dysfunction caused by infarction of central nervous system tissue (for example, haemorrhage may be a consequence of ischemic stroke, and in this situation, the stroke is an ischemic stroke with haemorrhagic transformation and not a haemorrhagic stroke). In some embodiments haemorrhagic stroke is defined as an acute episode of focal or global cerebral or spinal dysfunction caused by intraparenchymal, intraventricular, or subarachnoid haemorrhage.

"Hospitalisation for heart failure" may be defined as hospitalisation for at least 24 hours with a primary diagnosis of heart failure; wherein at least one of the following clinical manifestations of heart failure is present: Dyspnoea (dyspnoea with exertion, dyspnoea at rest, orthopnea, paroxysmal nocturnal dyspnoea), decreased exercise tolerance, fatigue, and other symptoms of worsened end-organ perfusion or volume overload; and wherein initiation or intensification of treatment specifically for heart failure including at least one of: a. augmentation in oral diuretic therapy, b. intravenous diuretic, inotrope, or vasodilator therapy, c. mechanical or surgical intervention (including: i. Mechanical circulatory support (e.g., intra-aortic balloon pump, ventricular assist device) or ii. Mechanical fluid removal (e.g., ultrafiltration, hemofiltration, dialysis)). Other symptoms of worsened end-organ perfusion or volume overload may include (i) at least TWO physical examination findings OR (ii) one physical examination finding and at least ONE laboratory criterion), including: a. Physical examination findings considered to be due to heart failure, including new or worsened: i. Peripheral oedema, ii. Increasing abdominal distention or ascites (in the absence of primary hepatic, disease), iii. Pulmonary rales/crackles/crepitations, iv. Increased jugular venous pressure and/or hepatojugular reflux, v. S3 gallop, vi. Clinically significant or rapid weight gain thought to be related to fluid retention; b. Laboratory evidence of new or worsening HF, if obtained within 24 hours of presentation, including: i. Increased B-type natriuretic peptide (BNP)/N-terminal pro-BNP (NT-proBNP) concentrations consistent with decompensation of heart failure (such as BNP>500 pg/mL or NT-proBNP>2,000 pg/mL), in patients with chronically elevated natriuretic peptides, a significant increase should be noted above baseline; ii. Radiological evidence of pulmonary congestion; iii. Non-invasive diagnostic evidence of clinically significant elevated left- or right-sided ventricular filling pressure or low cardiac output (for example, echocardiographic criteria could include: E/e'>15 or D-dominant pulmonary venous inflow pattern, plethoric inferior vena cava with minimal collapse on inspiration, or decreased left ventricular outflow tract (LVOT) minute stroke distance (time velocity integral (TVI))); OR iv. Invasive diagnostic evidence with right heart catheterization showing a pulmonary capillary wedge pressure (pulmonary artery occlusion pressure) 18 mmHg, central venous pressure 12 mmHg, or a cardiac index<2.2 L/min/$m^2$.

In some embodiments the methods of the present invention reduce the occurrence of an event. In some embodiments the methods of the present invention reduce the occurrence of an event compared to placebo.

Subject and Subpopulations

The subject to be administered semaglutide according to the present invention may be human, such as an adult human. In some embodiments said subjects are adults.

In some embodiments the subject to receive semaglutide administration according to the methods of the present invention has type 2 diabetes as well as (i) clinical evidence of cardiovascular disease, and/or (ii) subclinical evidence of cardiovascular disease. These cardiovascular diseases may be referred to as concomitant, i.e. one or more cardiovascular diseases are present in the subject at the same time as type 2 diabetes.

"Clinical evidence of cardiovascular disease" may be present when the subject fulfils at least one criterion selected from the group consisting of a) prior myocardial infarction,
b) prior stroke or transient ischaemic attack (TIA),
c) prior coronary, carotid or peripheral arterial revascularisation,
d) >50% stenosis on angiography or imaging of coronary, carotid or lower extremity arteries,
e) history of symptomatic coronary heart disease (e.g documented by eg positive exercise stress test or any cardiac imaging or unstable angina with ECG changes),
f) asymptomatic cardiac ischemia (e.g. documented by positive nuclear imaging test or exercise test or stress echo or any cardiac imaging),
g) heart failure New York Heart Association (NYHA) class and
h) chronic renal impairment (e.g. documented (prior to screening) by estimated glomerular filtration rate (eGFR)<60 mL/min/1.73 $m^2$ per MDRD).

In some embodiments clinical evidence of cardiovascular disease is prior myocardial infarction. In some embodiments clinical evidence of cardiovascular disease is prior stroke or transient ischaemic attack (TIA). In some embodiments clinical evidence of cardiovascular disease is prior coronary, carotid or peripheral arterial revascularisation. In some embodiments clinical evidence of cardiovascular disease is >50% stenosis on angiography or imaging of coronary, carotid or lower extremity arteries. In some embodiments clinical evidence of cardiovascular disease is history of symptomatic coronary heart disease (e.g. documented by positive exercise stress test or any cardiac imaging or unstable angina with ECG changes). In some embodiments clinical evidence of cardiovascular disease is asymptomatic cardiac ischemia (e.g. documented by positive nuclear imaging test or exercise test or stress echo or any cardiac imaging). In some embodiments clinical evidence of cardiovascular disease is heart failure New York Heart Association (NYHA) class II-III. In some embodiments clinical evidence of cardiovascular disease is chronic renal impairment (e.g., documented (prior to screening) by estimated glomerular filtration rate (eGFR)<60 mL/min/1.73 $m^2$ per MDRD).

"Subclinical evidence of cardiovascular disease" may be present when the subject fulfils at least one criterion selected from the group consisting of i) persistent microalbuminuria (e.g. 30-299 mg/g) or proteinuria,
j) hypertension and left ventricular hypertrophy by ECG or imaging,
k) left ventricular systolic or diastolic dysfunction (e.g. by imaging), and
l) ankle/brachial index<0.9.

In some embodiments subclinical evidence of cardiovascular disease is persistent microalbuminuria (30-299 mg/g) or proteinuria. In some embodiments subclinical evidence of cardiovascular disease is hypertension and left ventricular hypertrophy by ECG or imaging. In some embodiments subclinical evidence of cardiovascular disease is left ventricular systolic or diastolic dysfunction by imaging. In some embodiments subclinical evidence of cardiovascular disease is ankle/brachial index<0.9.

In some embodiments the term "prior" refers to before initiating administration of semaglutide.

In some embodiments characteristics of the subject described herein, such as BMI or age, refers to before initiating administration of semaglutide or at the time of initiating administration of semaglutide.

In some embodiments the subject is at least 50 years of age, such as at least 60 years of age. In some embodiments the subject is less than 60 years of age. In some embodiments the subject (i) is at least 50 years of age and has clinical evidence of cardiovascular disease, and/or (ii) is at least 60 years of age and has subclinical evidence of cardiovascular disease.

In some embodiments the subject has $HbA_{1c}$ of at least 7.0%, e.g. prior to receiving semaglutide administration. In some embodiments the subject has $HbA_{1c}$ of at least 9.0%, e.g. prior to receiving semaglutide administration. In some embodiments the subject has $HbA_{1c}$ in the range from 7.0% to 15.0%, e.g. prior to receiving semaglutide administration. $HbA_{1c}$ may be determined according to methods known in the art, for example as a percentage determined according to the method defined by the Diabetes Control and Complications Trial (DCCT), see New Engl J Med 1993; 329:977-986.

In some embodiments the subject is, except for semaglutide, anti-diabetic drug naive or treated with one or more oral anti-diabetic drugs (OADs) or treated with human NPH insulin or long-acting insulin analogue or premixed insulin, alone or in combination with one or two OAD(s). The subject may be anti-diabetic drug naive. The subject may be treated with one or more oral anti-diabetic drugs (OADs). The subject may be treated with human NPH insulin or long-acting insulin analogue or premixed insulin, alone or in combination with one or two OAD(s). In some embodiments the OAD may be selected from the group consisting of sulfonylureas, insulin secretagogues, thiazolidinediones, alpha-glucosidase inhibitors, dipeptidyl peptidase-4 inhibitors, sodium-glucose co-transporter-2 inhibitors, and combinations thereof. In some embodiments the OAD is sulfonylurea (e.g. glimepiride, glipizide, glyburide). In some embodiments the OAD is insulin secretagogues (e.g. biguanides such as metformin or meglitinides such as nateglinide). In some embodiments the OAD is thiazolidinediones (e.g. pioglitazone, rosiglitazone). In some embodiments the OAD is alpha-glucosidase inhibitors (e.g. acarbose, miglitol, voglibose). In some embodiments the OAD is sodium-glucose co-transporter-2 inhibitors (e.g. dapagliflozin, canagliflozin, empagliflozin). In some embodiments the OAD is dipeptidyl peptidase-4 inhibitors (e.g. sitagliptin). In some embodiments the OAD is not a dipeptidyl peptidase-4 inhibitor.

In some embodiments the subject has a BMI of no more than 30 kg/$m^2$, e.g. prior to receiving semaglutide administration. In some embodiments the subject does not have a BMI of at least 30 kg/$m^2$, e.g. prior to receiving semaglutide administration. BMI (body mass index) is a measure of body fat based on height and weight. The formula for calculation is BMI=(weight in kilograms)/(height in meters)$^2$. In some embodiments the subject has a BMI in the range of 30-50 kg/$m^2$.

In some embodiments the subject is male. In some embodiments the subject is not female. In some embodiments the subject is of Asian ethnic origin. In some embodiments the subject is not of ethnic origin other than Asian.

Heart failure exists in different degrees of severity. The most commonly used classification system of heart failure is the New York Heart Association Functional Classification (also referred to as "NYHA"). NYHA categorises subjects in one of four classes I-IV (Table A), based on their degree of limitation during physical activity, and optionally an additional subgroup A-D based on objective assessments, for further details see The Criteria Committee of the New York Heart Association. Nomenclature and Criteria for Diagnosis of Diseases of the Heart and Great Vessels. 9th ed. Boston, Mass: Little, Brown & Co; 1994:253-256). In some embodiments the subject has heart failure NYHA class I-III, such as class I, class II or class III.

TABLE A

NYHA class I-IV criteria

| NYHA Class | Functional Capacity of the subject |
|---|---|
| I | Subjects with cardiac disease but without resulting limitation of physical activity. Ordinary physical activity does not cause undue fatigue, palpitation, dyspnoea, or anginal pain. |
| II | Subjects with cardiac disease resulting in slight limitation of physical activity. They are comfortable at rest. Ordinary physical activity results in fatigue, palpitation, dyspnoea, or anginal pain. |
| III | Subjects with cardiac disease resulting in marked limitation of physical activity. They are comfortable at rest. Less than ordinary activity causes fatigue, palpitation, dyspnoea, or anginal pain. |
| IV | Subjects with cardiac disease resulting in inability to carry on any physical activity without discomfort. Symptoms of heart failure or the anginal syndrome may be present even at rest. If any physical activity is undertaken, discomfort is increased. |

In some embodiments the subject has no heart failure or has heart failure NYHA class I, e.g. prior to receiving semaglutide administration. In some embodiments the subject has heart failure or has heart failure NYHA class I, e.g. prior to receiving semaglutide administration. In some embodiments the subject does not have heart failure NYHA class II or III, e.g. prior to receiving semaglutide administration. In some embodiments the subject does not have heart failure NYHA class II, III or IV, e.g. prior to receiving semaglutide administration.

Estimated glomerular filtration rate (eGFR) may be calculated based on serum creatinine concentration followed by either the equation Modification of Diet in Renal Disease (MDRD) or the Chronic Kidney Disease Epidemiology Collaboration (CKD-EPI), both involving variables for age, gender, and ethnic origin of the subject. eGFR determined by MDRD may be referred to as eGFR-MDRD. eGFR determined by CKD-EPI may be referred to as eGFR-CKD-EPI. The eGFR-MDRD equation may be as defined in formula V: eGFR ($mL/min/1.73\ m^2$)$=175\times(S_{cr})^{-1.154}\times(Age)^{-0.203}\times$(0.742 if female)×(1.212 if African American) [V]. The CKD-EPI equation may be as defined in formula VI: eGFR$=141\times min^{\alpha}\times max^{-1.209}\times 0.993^{Age}\times$(1.018 if female)×(1.159 if black) [VI], wherein "min" indicates the minimum of $S_{cr}/\kappa$ or 1, "max" indicates the maximum of $S_{cr}/\kappa$ or 1, $S_{cr}$ is serum creatinine in mg/dL, κ is 0.7 for females and 0.9 for males, and α is −0.329 for females or −0.411 for males. The glomerular filtration rate may alternatively be determined by the "Cockroft-Gault formula" may be as defined by Formula III: CrCl (mL/min)=(N×[140-age (years)]×weight*(kg))/Serum creatinine (μM) [III], wherein CrCl is the Cockcroft and Gault creatinine clearance, wherein N is 1.23 for males and 1.04 for females, and wherein if actual weight is greater than 120% IBW then weight is the ideal body weight (IBW) as defined in Formula IIIa: IBW (kg)=(no of inches over 5 ft×2.3)+M [IIIa], wherein M is 50 for males and 45.5 for females.

In some embodiments the subject does not have type 1 diabetes.

In some embodiments the subject does not receive administration of a GLP-1 receptor agonist (exenatide, liraglutide or other) or pramlintide prior to initiating administration of semaglutide according to the present invention, such as within 100 days or within 104 days prior to this initiation.

In some embodiments the subject does not receive administration of a DPP-IV inhibitor prior to initiating administration of semaglutide according to the present invention, such as within 30 days or within 44 days prior to this initiation.

In some embodiments the subject does not receive administration of insulin other than basal and pre-mixed insulin (except for short-term use in connection with intercurrent illness) prior to initiating administration of semaglutide according to the present invention, such as within 90 days or within 104 days prior to this initiation.

In some embodiments the subject does not have acute decompensation of glycaemic control requiring immediate intensification of treatment to prevent acute complications of diabetes (eg diabetes ketoacidosis) prior to initiating administration of semaglutide according to the present invention, such as within 90 days or 104 days prior to this initiation.

In some embodiments the subject does not have a history of chronic pancreatitis or idiopathic acute pancreatitis prior to initiating administration of semaglutide according to the present invention.

In some embodiments the subject does not have acute coronary or cerebrovascular event within 90 days prior to initiating administration of semaglutide according to the present invention.

In some embodiments the subject does not have currently planned coronary, carotid or peripheral artery revascularisation prior to initiating administration of semaglutide according to the present invention.

In some embodiments the subject does not have heart failure NYHA class IV prior to initiating administration of semaglutide according to the present invention.

In some embodiments the subject does not have chronic haemodialysis or chronic peritoneal dialysis prior to initiating administration of semaglutide according to the present invention.

In some embodiments the subject does not have end stage liver disease prior to initiating administration of semaglutide according to the present invention. "End stage liver disease" may be defined as the presence of acute, or chronic liver disease and recent history of one or more of the following: ascites, encephalopathy, variceal bleeding, bilirubin 2.0 mg/dL, albumin level g/dL, prothrombin time seconds prolonged, international normalised ratio (INR) or prior liver transplant.

In some embodiments the subject has not had a prior solid organ transplant or is not awaiting solid organ transplant prior to initiating administration of semaglutide according to the present invention.

In some embodiments the subject does not have a diagnosis of malignant neoplasm in the previous 5 years (except basal cell skin cancer or squamous cell skin cancer) prior to initiating administration of semaglutide according to the present invention.

In some embodiments the subject does not have a personal or family history of multiple endocrine neoplasia type 2 or familial medullary thyroid carcinoma prior to initiating administration of semaglutide according to the present invention.

In some embodiments the subject does not have a personal history of non-familial medullary thyroid carcinoma prior to initiating administration of semaglutide according to the present invention.

In some embodiments the subject does not have calcitonin 50 ng/L within 2 weeks prior to initiating administration of semaglutide according to the present invention.

In some embodiments the subject does not simultaneously participate in any other clinical trial of an investigational agent, expect for participation in a clinical trial with investigational stent(s).

In some embodiments the subject does not receive administration of any investigational medicinal product (IMP) within 45 days prior to initiating administration of semaglutide according to the present invention.

In some embodiments the subject is not female of child-bearing potential who is pregnant, breast-feeding or intends to become pregnant prior to initiating administration of semaglutide according to the present invention.

Semaglutide

Semaglutide is the GLP-1 receptor agonist $N^{6.26}$-{18-[N-(17-carboxy-heptadecanoyl)-L-γ-glutamyl]-10-oxo-3,6,12,15-tetraoxa-9,18-diazaoctadecanoyl}-[8-(2-amino-2-propanoic acid),34-L-arginine]human glucagon-like peptide 1(7-37), its structure is shown in Chem (I). Semaglutide may also be referred to as N-epsilon26-[2-(2-{2-[2-(2-{2-[(S)-4-Carboxy-4-(17-carboxyheptadecanoylamino)butyrylamino]ethoxy}ethoxy)acetylamino]ethoxy}ethoxy)acetyl][Aib8, Arg34]GLP-1-(7-37). Semaglutide may be prepared as described in Example 4 of WO2006/097537.

maceutically acceptable excipients, such as one or more selected from the group consisting of a buffer, an isotonic agent, and a preservative. The formulation of pharmaceutically active ingredients with various excipients is known in the art, see e.g. Remington: The Science and Practice of Pharmacy (e.g. 19th edition (1995), and any later editions). The term "excipient" broadly refers to any component other than the active therapeutic ingredient(s), e.g. semaglutide. The excipient may be an inert substance, an inactive substance, and/or a not medicinally active substance.

In some embodiments the pharmaceutical composition comprises a phosphate buffer, such as a sodium phosphate buffer, e.g. disodium phosphate. In some embodiments the pharmaceutical composition comprises an isotonic agent, such as propylene glycol. In some embodiments the pharmaceutical composition comprises a preservative, such as phenol.

The pharmaceutical composition may be in the form of a solution or a suspension. In some embodiments the pharmaceutical composition is aqueous composition, such as an aqueous solution or an aqueous suspension. The term "aqueous composition" is defined as a composition comprising at least 50% w/w water. Likewise, the term "aqueous solution" is defined as a solution comprising at least 50% w/w water, and the term "aqueous suspension" is defined as a suspension comprising at least 50% w/w water. An aqueous composition may comprise at least 50% w/w water, or at least 60%, 70%, 80%, or even at least 90% w/w of water. In some embodiments the pharmaceutical composition has a pH in the range of 7.0-9.0, such as 7.0-8.5.

In some embodiments semaglutide is administered in the form of a pharmaceutical composition comprising about 0.1-20 mg/ml semaglutide, about 2-15 mM phosphate buffer, about 2-25 mg/ml propylene glycol, about 1-18 mg/ml phenol, and has a pH in the range of 7.0-9.0. In some embodiments semaglutide is administered in the form of a pharmaceutical composition comprising about 1.34 mg/ml semaglutide, about 1.42 mg/ml disodium phosphate dihydrate, about 14.0 mg/ml propylene glycol, about 5.5 mg/ml phenol, and has pH of about 7.4. In some embodiments semaglutide is administered in the form of a pharmaceutical composition comprising 1.34 mg/ml semaglutide, 1.42 mg/ml disodium phosphate dihydrate, 14.0 mg/ml propylene glycol, 5.5 mg/ml phenol, and has pH of 7.4.

Chem (I)

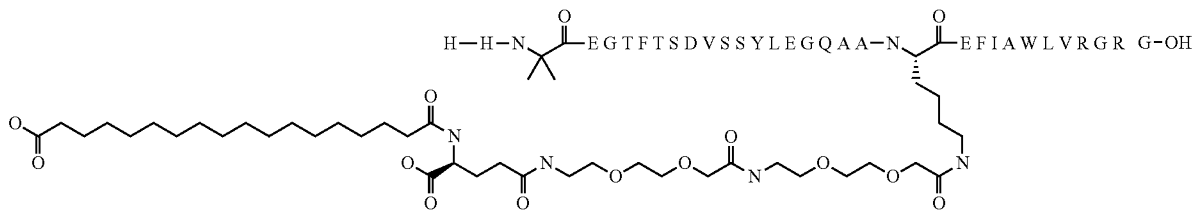

Pharmaceutical Composition

Semaglutide may be administered in the form of a pharmaceutical composition. The pharmaceutical composition may comprise semaglutide in a concentration from 0.1 mg/ml to 100 mg/ml. In some embodiments the pharmaceutical composition comprises 0.01-50 mg, or 0.01-20 mg, or 0.01-10 mg/ml semaglutide. In some embodiments the pharmaceutical composition comprises 0.1-20 mg/ml semaglutide.

The pharmaceutical compositions described herein may further comprise one or more pharmaceutically acceptable excipients, for example selected from the group consisting of buffer system, preservative, tonicity agent, chelating agent, stabilizer and surfactant. In some embodiments the pharmaceutical composition comprises one or more phar- Administration Regimen Semaglutide may be administered in a therapeutically effective amount, such as an amount therapeutically effective to treat type 2 diabetes. The therapeutically effective amount of semaglutide can be assessed by a medical doctor. The dosage of semaglutide may be in the range from 0.01 to 10 mg.

Semaglutide may be administered once weekly or more frequent, such as once daily. In some embodiments semaglutide is administered at any time in the day. In some embodiments the dosage of semaglutide is in the range from 0.1 to 5.0 mg, such as in the range from 0.1 to 3.0 mg. In some embodiments the daily dosage of semaglutide is selected from the group consisting of 0.5 and 1.0 mg.

In some embodiments the term "chronic treatment" as used herein with reference to semaglutide means administration in an amount and frequency to provide a therapeutic effect. In some embodiments the term "chronic treatment" as used herein with reference to semaglutide means once weekly administration of 0.1-3.0 mg, such as 0.5 or 1.0 mg, semaglutide. In some embodiments the term "chronic treatment" as used herein with reference to semaglutide means once daily administration of 0.05-0.3 mg, such as 0.05, 0.1, 0.2, or 0.3 mg, semaglutide.

In some embodiments semaglutide is administered in an amount in the range of 0.05-2.0 mg per week, such as 0.5 or 1.0 mg per week, optionally by once weekly administration. In some embodiments semaglutide is administered in an amount of at least 0.1 mg per week, such as at least 0.2 mg per week or at least 0.3 mg per week, optionally by once weekly administration. In some embodiments semaglutide is administered in an amount of no more than 1.8 mg per week, such as no more than 1.6 mg per week or no more than 1.4 mg per week, optionally by once weekly administration. In some embodiments semaglutide is administered once weekly in an amount of 0.5 or 1.0 mg. In some embodiments semaglutide is administered in an amount less than 0.7 mg per week, such as in the range of 0.05-0.7 mg per week, optionally by once weekly administration.

Semaglutide may be administered via parenteral administration, for example subcutaneous injection. Semaglutide may be administered using a pen-injector, such as a 3 ml disposable pen-injector.

The term "chronic treatment" as used herein may refer to administration of a drug according to a prescribed dosage regimen (for example once weekly administration) for a long period of time (for example at least 2 years or at least 5 years) wherein up to 10%, such as up to 5%, of dosages may be missed; provided that no more than 10 consecutive dosages are missed.

Unless otherwise stated, ranges herein include their end points. In some embodiments the term "a" means "one or more". In some embodiments, and unless otherwise indicated in the specification, terms presented in singular form also include the plural situation. Herein the term "about" means ±10% of the value referred to, and includes the value.

Non-Limiting Embodiments of the Invention

Non-limiting embodiments of the invention include:

1. A method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method delays or reduces major adverse cardiovascular event (MACE).
2. A method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method delays or reduces non-fatal MI.
3. A method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method delays or reduces non-fatal stroke.
4. A method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method delays or reduces revascularisation.
5. A method of treating type 2 diabetes, comprising administering semaglutide in a therapeutically effective amount to a subject in need thereof, wherein said subject has clinical evidence of cardiovascular disease and/or subclinical evidence of cardiovascular disease; wherein said method delays or reduces hospitalisation for unstable angina pectoris.
6. A method of reducing the risk of MACE in subjects with type 2 diabetes mellitus and high cardiovascular risk.
7. A method of reducing the risk of MACE in subjects with type 2 diabetes mellitus and high cardiovascular risk, wherein said MACE is selected from the group consisting of non-fatal MI, non-fatal stroke, CV death caused by MI, and CV death caused by stroke.
8. A method of delaying myocardial infarction or stroke in subjects with type 2 diabetes mellitus and high cardiovascular risk.
9. A method of preventing cardiovascular events in subjects with type 2 diabetes, wherein said "cardiovascular events" is one or more major adverse cardiovascular events, and wherein "major adverse cardiovascular event" is as defined herein.
10. The method according to any one of the preceding embodiments, wherein said method delays or reduces non-fatal MI, non-fatal stroke, revascularisation, or hospitalisation for unstable angina pectoris.
11. The method according to any one of the preceding embodiments, wherein said MACE is selected from the group consisting of CV death, non-fatal MI, non-fatal stroke, revascularisation, hospitalisation for heart failure, and hospitalisation for unstable angina pectoris, and wherein MACE is reduced or delayed by from about 20% to about 35% compared to placebo, such as reduced about 27% compared to placebo.
12. The method according to any one of the preceding embodiments, wherein said MACE is selected from the group consisting of CV death, non-fatal MI, and non-fatal stroke, and wherein said MACE is reduced by from about 20% to about 30% compared to placebo, such as reduced about 26% compared to placebo.
13. The method according to any one of the preceding embodiments, wherein said MACE is non-fatal MI, and wherein said non-fatal MI is reduced or delayed (i) by from about 15% to about 35% compared to placebo, or (ii) by about 26% compared to placebo.
14. The method according to any one of the preceding embodiments, wherein said MACE is non-fatal stroke, and wherein said non-fatal stroke is reduced or delayed (i) by from about 30% to about 50% compared to placebo, or (ii) by about 39% compared to placebo.
15. The method according to any one of the preceding embodiments, wherein said MACE is revascularisation, and wherein said Revascularisation is reduced or delayed (i) by from about 30% to about 50% compared to placebo, or (ii) by about 38% compared to placebo.
16. The method according to any one of the preceding embodiments, wherein said MACE is hospitalisation for unstable angina pectoris, and wherein said hospitalisation for unstable angina pectoris is reduced or delayed (i) by from about 10% to about 30% compared to placebo, or (ii) by about 18% compared to placebo.

17. The method according to any one of the preceding embodiments, wherein said subject has a BMI of no more than 30 $kg/m^2$.

18. The method according to any one of the preceding embodiments, wherein said subject does not have a BMI of more than 30 $kg/m^2$.

19. The method according to any one of the preceding embodiments, wherein said subject does not have heart failure NYHA class II or III.

20. The method according to any one of the preceding embodiments, wherein said subject does not have heart failure NYHA class II, III, or IV.

21. The method according to any one of the preceding embodiments, wherein said subject has no heart failure or has heart failure NYHA class I.

22. The method according to any one of the preceding embodiments, wherein said subject has heart failure or has heart failure NYHA class I.

23. The method according to any one of the preceding embodiments, wherein said subject is male.

24. The method according to any one of the preceding embodiments, wherein said subject is not female.

25. The method according to any one of the preceding embodiments, wherein said subject is of Asian ethnic origin.

26. The method according to any one of the preceding embodiments, wherein said subject is not of ethnic origin other than Asian.

27. The method according to any one of the preceding embodiments, wherein said administration of semaglutide is a chronic treatment in which semaglutide is administered for at least 16 months, such as at least 30 months, and wherein said method reduces or delays non-fatal myocardial infarction (MI).

28. The method according to any one of the preceding embodiments, wherein said administration of semaglutide is a chronic treatment in which semaglutide is administered for at least 18 months, such as at least 30 months, and wherein said method reduces or delays revascularisation.

29. The method according to any one of the preceding embodiments, wherein said MACE is the first MACE after initiating administration of semaglutide.

30. The method according to any one of the preceding embodiments, wherein semaglutide is administered in an amount in the range of 0.05-2.0 mg per week, such as 0.5 or 1.0 mg per week, optionally by once weekly administration.

31. The method according to any one of the preceding embodiments, wherein semaglutide is administered in the form of a pharmaceutical composition comprising about 1-20 mg/ml semaglutide, about 2-15 mM phosphate buffer, about 2-25 mg/ml propylene glycol, about 1-18 mg/ml phenol, and has a pH in the range of 7.0-9.0.

32. The method according to any one of the preceding claims, wherein semaglutide is administered in the form of a pharmaceutical composition comprising about 1-20 mg/ml semaglutide, and having a pH in the range of 7.0-9.0.

33. The method according to any one of the preceding embodiments, wherein the dosage of semaglutide is in the range from 0.1 to 5.0 mg.

34. The method according to any one of the preceding embodiments, wherein semaglutide is administered once weekly in an amount of 0.5 or 1.0 mg.

EXAMPLES

List of Abbreviations

MACE: Major adverse cardiovascular event $HbA_{1c}$: Glycosylated haemoglobin

GLP-1: Glucagon-like peptide-1

BMI: Body mass index

N: Number of subjects

CV: Cardiovascular

OAD: Oral antidiabetic drug

TIA: Transient ischaemic attack

CI: Confidence interval

CKD-EPI: Chronic Kidney Disease Epidemiology Collaboration

MDRD: modification of diet in renal disease

MI: Myocardial infarction.

UAP: Unstable angina pectoris.

Clinical Trial: Materials and Methods

A long-term randomised, double-blind, placebo-controlled, four-armed parallel-group, multicentre, multi-national, safety and efficacy trial was carried out to evaluate cardiovascular and other long-term outcomes with semaglutide in 3,297 human subjects with type 2 diabetes. Subject inclusion and exclusion criteria were as described in Table 2.

The subjects were randomised to receive once weekly treatment doses of 0.5 mg semaglutide, 1.0 mg semaglutide, or volume-matched placebo, as an add-on to their standard-of-care treatment, wherein administration started with an initial dose escalation step at 0.25 mg semaglutide once weekly for 4 weeks, and for the 1.0 mg semaglutide group an additional 4 week period at 0.5 mg semaglutide once weekly, or their volume-matched placebo, as shown in Table 1. Additional glucose-lowering medications were allowed to be added to the anti-diabetic regimen to maintain target glycaemic control at the discretion of investigator.

Semaglutide was administered in the form of an aqueous solution comprising semaglutide or placebo, both using a 3 ml disposable pen-injector. This pen-injector was identical for the semaglutide and placebo administrations. This aqueous solution contained 1.34 mg/ml semaglutide, 1.42 mg/ml disodium phosphate dihydrate, 14.0 mg/ml propylene glycol, 5.5 mg/ml phenol, at pH 7.40. Semaglutide may be prepared as described in Example 4 of WO2006/097537.

Injections were administered in the thigh, abdomen or upper arm, at any time of day irrespective of meals. The injections were administered on the same day of the week during the trial.

TABLE 1

Trial design: Amount of semaglutide or its equivalent volume of placebo administered once weekly at different stages of the trial

| | Duration of period (weeks) | | | | | |
|---|---|---|---|---|---|---|
| Treatment arm | 2 | | 4 | 4 | 96-135 | 5 |
| Semaglutide | Screening | Randomisation | 0.25 mg | 0.5 mg | | Follow-up |
| 0.5 mg | | | 190 µl | 370 µl | | |
| Semaglutide placebo | | | 0.25 mg | 0.5 mg | | |
| 0.5 mg | | | 190 µl | 370 µl | | |
| Semaglutide | | | 0.25 mg | 0.5 mg | 1.0 mg | |
| 1.0 mg | | | 190 µl | 370 µl | 740 µl | |
| Semaglutide placebo | | | 0.25 mg | 0.5 mg | 1.0 mg | |
| 1.0 mg | | | 190 µl | 370 µl | 740 µl | |

TABLE 2

Subject inclusion and exclusion criteria (all inclusion criteria were fulfilled for eligible subjects; one or more exclusion criteria were fulfilled for subjects to be excluded)

| | Definiiton |
|---|---|
| Inclusion Criteria | Men or women with type 2 diabetes. |
| | Age ≥50 years at screening and clinical evidence of cardiovascular disease, OR age ≥60 years at screening and subclinical evidence of cardiovascular disease. |
| | $HbA_{1c}$ ≥7.0% at screening. |
| | Anti-diabetic drug naive or treated with one or more oral anti-diabetic drugs (OADs) or treated with human NPH insulin or long-acting insulin analogue or premixed insulin, alone or in combination with one or two OAD(s). |
| Exclusion Criteria | Type 1 diabetes. |
| | Use of a GLP-1 receptor agonist (exenatide, liraglutide or other) or pramlintide within 90 days prior to screening (trial start). |
| | Use of any DPP-IV (dipeptidyl peptidase IV) inhibitor within 30 days prior to screening. |
| | Use of insulin other than basal and pre-mixed insulin within 90 days prior to screening - except for short-term use in connection with intercurrent illness |
| | Acute decompensation of glycaemic control requiring immediate intensification of treatment to prevent acute complications of diabetes (eg diabetes ketoacidosis) within 90 days prior to screening |
| | History of chronic pancreatitis or idiopathic acute pancreatitis |
| | Acute coronary or cerebrovascular event within 90 days prior to randomisation. |
| | Currently planned coronary, carotid or peripheral artery revascularisation. |
| | Heart failure NYHA class IV. |
| | Chronic haemodialysis or chronic peritoneal dialysis. |
| | End stage liver disease, defined as the presence of acute, or chronic liver disease and recent history of one or more of the following: ascites, encephalopathy, variceal bleeding, bilirubin ≥2.0 mg/dL, albumin level ≤3.5 g/dL, prothrombin time ≥4 seconds prolonged, international normalised ratio (INR) ≥1.7 or prior liver transplant. |
| | A prior solid organ transplant or awaiting solid organ transplant. |
| | Diagnosis of malignant neoplasm in the previous 5 years (except basal cell skin cancer or squamous cell skin cancer). |
| | Personal or family history of multiple endocrine neoplasia type 2 or familial medullary thyroid carcinoma. |
| | Personal history of non-familial medullary thyroid carcinoma. |
| | Calcitonin ≥50 ng/L at screening. |
| | Simultaneous participation in any other clinical trial of an investigational agent. Participation in a clinical trial with investigational stent(s) is allowed. |
| | Receipt of any investigational medicinal product (IMP) within 30 days prior to screening or according to local requirements, if longer. |
| | Female of childbearing potential who is pregnant, breast-feeding or intends to become pregnant or is not using an adequate contraceptive method (adequate contraceptive measure as required by local regulation or practice). |

In this trial, "clinical evidence of cardiovascular disease" was present when the subject fulfilled at least one criterion selected from the group consisting of a) to h):

a) prior myocardial infarction,
b) prior stroke or transient ischaemic attack,
c) prior coronary, carotid or peripheral arterial revascularisation,
d) >50% stenosis on angiography or imaging of coronary, carotid or lower extremity arteries,
e) history of symptomatic coronary heart disease (documented by e.g. positive exercise stress test or any cardiac imaging or unstable angina with ECG changes),
f) asymptomatic cardiac ischemia (e.g. documented by positive nuclear imaging test or exercise test or stress echo or any cardiac imaging),
g) heart failure New York Heart Association (NYHA) class and
h) chronic renal impairment (documented (prior to screening) by estimated glomerular filtration rate (eGFR)<60 mL/min/1.73 $m^2$ per MDRD).

In this trial, "subclinical evidence of cardiovascular disease" was present when the subject fulfilled at least one criterion selected from the group consisting of i) to l):

i) persistent microalbuminuria (30-299 mg/g) or proteinuria,
j) hypertension and left ventricular hypertrophy by ECG or imaging,
k) left ventricular systolic or diastolic dysfunction by imaging, and
l) ankle/brachial index<0.9.

Baseline characteristics of subjects are shown in Table 3.

TABLE 3

| Baseline characteristics | Semaglutide | Placebo |
|---|---|---|
| Age (year)[a] | 64.7 [50; 89] | 64.6 [50; 88] |
| Sex (N, %) | | |
| Female | 635 (38.5) | 660 (40.0) |
| Male | 1013 (61.5) | 989 (60.0) |
| Ethnic origin (N, %) | | |
| White | 1384 (84.0) | 1352 (82.0) |
| Black or African-American | 108 (6.6) | 113 (6.9) |
| Asian | 121 (7.3) | 152 (9.2) |
| Other | 35 (2.1) | 32 (1.9) |
| Body weight (kg)[a] | 92.4 [40.7; 192] | 91.9 [40.7; 217] |
| BMI ($kg/m^2$)[a] | 32.8 [19.3; 77.7] | 32.8 [17.6; 61.4] |
| Diabetes duration (years) | 14.2 [0.10; 49.9] | 13.6 [0.10; 53.9] |
| HbA1c (%) | 8.70 [6.60; 17.9] | 8.70 [5.90; 15.2] |
| FPG (mmol/L) | 10.2 [2.50; 40.2] | 10.3 [2.90; 30.7] |
| CV risk factors | | |
| Systolic blood pressure (mmHg)[a] | 136 [84; 203] | 135 [74; 204] |
| Diastolic blood pressure (mmHg)[a] | 77.0 [46; 116] | 77.1 [40; 110] |
| Pulse (bpm)[a] | 72.12 [42; 149] | 72.0 [40; 117] |

TABLE 3-continued

| Baseline characteristics | Semaglutide | Placebo |
|---|---|---|
| LDL cholesterol (mmol/L)[a] | 2.14 [0.12; 10.31] | 2.13 [0.07; 10.31] |
| HDL cholesterol (mmol/L)[a] | 1.13 [0.43; 2.88] | 1.13 [0.44; 3.51] |
| Never smoked[b] | 754 (45.8) | 739 (44.8) |
| eGFR (MDRD) (mL/min/1.73 $m^2$)[a] | 70.9 [8.00; 163] | 70.9 [8.00; 198] |
| Normal (≥90)[b] | 493 (29.9) | 497 (30.1) |
| Mild renal impairment (60-<90)[b] | 686 (41.6) | 682 (41.4) |
| Moderate renal impairment (30-<60)[b] | 423 (25.7) | 409 (24.8) |
| Severe renal impairment (15-<30)[b] | 41 (2.5) | 54 (3.3) |
| End stage renal impairment (<15)[b] | 5 (0.3) | 7 (0.4) |
| History of cardiovascular disease | | |
| Ischaemic heart disease | 988 (60.0) | 1006 (61.0) |
| Myocardial infarction | 530 (32.2) | 542 (32.9) |
| Heart failure | 381 (23.1) | 396 (24.0) |
| Ischaemic stroke | 178 (10.8) | 205 (12.4) |
| Haemorrhagic stroke | 52 (3.2) | 56 (3.4) |
| Transient ischaemic attack | 98 (5.9) | 94 (5.7) |
| Hypertension | 1543 (93.6) | 1516 (91.9) |
| Evidence of cardiovascular disease | | |
| Clinical evidence of CV disease, age ≥50 | 1353 (82.1) | 1382 (83.8) |
| Subclinical evidence CV disease, age ≥60 | 295 (17.9) | 267 (16.2) |

[a]Arithmetric mean and [min; max].
[b]number of subjects (N) and percentage (%).

The term "placebo" as used herein refers to a formulation identical to the semaglutide formulation except not comprising semaglutide and the placebo was administered in the volume used in the equivalent semaglutide dosage.

The term "baseline" herein (e.g. used as part of "baseline characteristics" or "baseline cardiovascular risk profile") may refer to the level of a certain parameter (e.g. level of HbA1c) by the determination made in connection with the medical visit at the time of randomisation of the subject. In some embodiments the term baseline refers to a parameter before initiating administration of semaglutide, e.g. the history of a certain event in a subject.

The results of this trial may be presented herein as a number or fraction of subjects experiencing an event. Alternatively, the results of this trial may be presented with hazard ratios estimated in a Cox proportional hazard model, which is the standard statistical model used for estimating time to an event. The term "hazard ratio" (also referred to as "HR") as used herein means the instantaneous risk ratio of experiencing an event when administered semaglutide compared to placebo which are the two treatments in this trial. An upper limit of the 95% confidence interval (CI) for the HR of less than 1.00 means that the estimated treatment ratio between semaglutide and placebo with respect to the event of interest is statistically significant in favour of semaglutide on a 5% significance level. A 5% significance level is the standard level for investigating significance in clinical trials.

Figure 2:
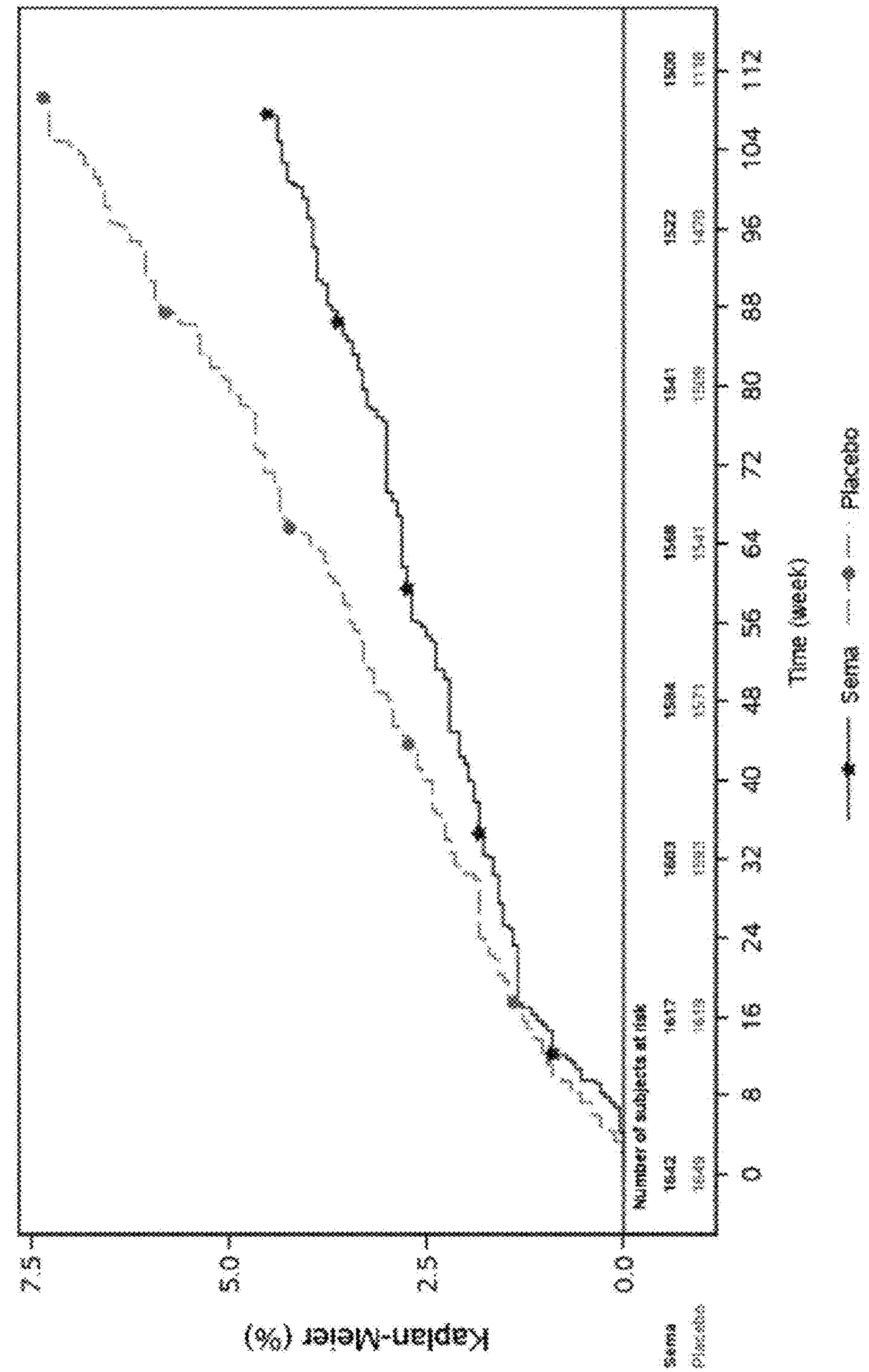
FIG. 2 shows time from randomisation to first revascularisation following administration of semaglutide (Sema) or its placebo.

Trial results with respect to MACE effects are shown in Tables 4, 5 and 6. FIG. 1 shows time to first non-fatal myocardial infarction in a Kaplan-Meier plot. FIG. 2 shows time to first revascularisation. The results in FIG. 1 and FIG. 2 show that semaglutide has particularly good effect in delaying non-fatal myocardial infarction or revascularisation after a certain period of chronic treatment.

TABLE 4

Time to first MACE selected from the group consisting of cardiovascular death, non-fatal myocardial infarction, or non-fatal stroke, revascularization (coronary and peripheral), hospitalisation for unstable angina pectoris (UAP), and hospitalisation for heart failure

| | Hazard ratio | Semaglutide | | Placebo | |
|---|---|---|---|---|---|
| | [95% CI] | N | % | N | % |
| First MACE* | 0.74 [0.62; 0.89] | 199 | 12.1 | 264 | 16.0 |
| Individual components of MACE* | | | | | |
| Myocardial infarction, non-fatal | 0.74 [0.51; 1.08] | 47 | 2.9 | 64 | 3.9 |
| Stroke, non-fatal | 0.61 [0.38; 0.99] | 27 | 1.6 | 44 | 2.7 |
| Cardiovascular death | 0.98 [0.65; 1.48] | 44 | 2.7 | 46 | 2.8 |
| Revascularisation | 0.65 [0.50; 0.86] | 83 | 5.0 | 126 | 7.6 |
| Coronary revascularisation | 0.68 [0.50; 0.92] | 70 | 4.2 | 103 | 6.2 |
| Peripheral revascularisation | 0.63 [0.34; 1.19] | 16 | 1.0 | 25 | 1.5 |
| Hospitalisation for UAP | 0.82 [0.47; 1.44] | 22 | 1.3 | 27 | 1.6 |
| Hospitalisation for heart failure | 1.11 [0.77; 1.61] | 59 | 3.6 | 54 | 3.3 |

Cox proportional hazard model adjusted for treatment.

N: Number of subjects experiencing at least one event.

%: Percentage of subjects experiencing at least one event.

*In this table the term "MACE" refers to an event selected from the group consisting of cardiovascular death, non-fatal myocardial infarction, or non-fatal stroke, revascularization (coronary and peripheral), hospitalisation for unstable angina pectoris (UAP), and hospitalisation for heart failure.

TABLE 5

Time to first MACE in subgroups, wherein MACE is selected from the group consisting of cardiovascular death, non-fatal MI, and non-fatal stroke

| Factor | Hazard ratio [95% CI] | Semaglutide N | Semaglutide % | Placebo N | Placebo % |
|---|---|---|---|---|---|
| First MACE* | 0.74 [0.58; 0.95] | 108 | 6.6 | 146 | 8.9 |
| Myocardial infarction, non-fatal | | 46 | 2.8 | 64 | 3.9 |
| Stroke, non-fatal | | 25 | 1.5 | 42 | 2.5 |
| Cardiovascular death | | 37 | 2.2 | 40 | 2.4 |
| Sex | | | | | |
| Female | 0.84 [0.54; 1.31] | 35 | 5.5 | 43 | 6.5 |
| Male | 0.68 [0.50; 0.92] | 73 | 7.2 | 103 | 10.4 |
| BMI | | | | | |
| ≤30 $kg/m^2$ | 0.58 [0.39; 0.87] | 39 | 6.6 | 64 | 11.0 |
| >30 $kg/m^2$ | 0.84 [0.61; 1.16] | 69 | 6.6 | 82 | 7.7 |

TABLE 5-continued

Time to first MACE in subgroups, wherein MACE is selected from the group consisting of cardiovascular death, non-fatal MI, and non-fatal stroke

| Factor | Hazard ratio [95% CI] | Semaglutide N | Semaglutide % | Placebo N | Placebo % |
|---|---|---|---|---|---|
| Ethnic origin | | | | | |
| Asian | 0.58 [0.25; 1.34] | 2 | 5.7 | 4 | 12.5 |
| White | 0.76 [0.58; 1.00] | 8 | 6.6 | 17 | 11.2 |
| Black or African-American | 0.72 [0.23; 2.28] | 5 | 4.6 | 7 | 6.2 |
| Other | 0.46 [0.08; 3.50] | 93 | 6.7 | 118 | 8.7 |
| Heart failure subgroups | | | | | |
| Heart failure NYHA class I or no heart failure | 0.64 [0.48; 0.86] | 73 | 5.4 | 112 | 8.2 |
| Heart failure NYHA class II or III | 1.03 [0.64; 1.66] | 35 | 12.3 | 34 | 11.8 |

Cox proportional hazard model adjusted for treatment.

N: Number of subjects experiencing at least one event.

%: Percentage of subjects experiencing at least one event.

*In this table the term "MACE" refers to an event selected from the group consisting of cardiovascular death, non-fatal myocardial infarction, or non-fatal stroke.

TABLE 6

Time to first MACE in subgroups, wherein MACE is selected from the group consisting of cardiovascular death, non-fatal MI, and non-fatal stroke in each treatment arm of the trial

| | Hazard ratio [95% CI] | Semaglutide (N) | Placebo (N) |
|---|---|---|---|
| First MACE* 0.5 mg semaglutide | 0.77 [0.55; 1.08] | 59 | 77 |
| First MACE* 1.0 mg semaglutide | 0.71 [0.49; 1.02] | 49 | 69 |

Cox proportional hazard model adjusted for treatment.

N: Number of subjects experiencing at least one event.

%: Percentage of subjects experiencing at least one event.

*In this table the term "MACE" refers to an event selected from the group consisting of cardiovascular death, non-fatal myocardial infarction, or non-fatal stroke.

These results show that semaglutide has a surprisingly good effect on reducing cardiovascular disease and that this effect is even more pronounced in some subgroups.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method of reducing the risk of a major adverse cardiovascular event (MACE) in a subject in need thereof, wherein the method comprises administering to the subject a pharmaceutical composition comprising semaglutide in an amount of 0.05-2.0 mg once weekly by subcutaneous injection;

wherein the subject has type 2 diabetes and cardiovascular disease; and wherein the MACE is selected from the group consisting of cardiovascular (CV) death, non-fatal myocardial infarction (MI), and non-fatal stroke.

2. The method according to claim 1, wherein the cardiovascular disease is selected from the group consisting of clinical evidence of cardiovascular disease and subclinical evidence of cardiovascular disease;

wherein the clinical evidence of cardiovascular disease is selected from the group consisting of prior myocardial infarction, prior stroke or transient ischaemic attack; prior coronary, carotid, or peripheral arterial revascularization; >50% stenosis on angiography or imaging of coronary, carotid, or lower extremity arteries; history of symptomatic coronary heart disease; asymptomatic cardiac ischemia; heart failure; and chronic renal impairment by estimated glomerular filtration rate<60 mL/min/1.73 $m^2$ per modification of diet in renal disease (MDRD); and wherein the subclinical evidence of cardiovascular disease is selected from the group consisting of persistent microalbuminuria or proteinuria; hypertension and left ventricular hypertrophy by electrocardiogram (ECG) or imaging; left ventricular systolic or diastolic dysfunction; and ankle/brachial index<0.9.

3. The method according to claim 1, wherein the subject has a body mass index (BMI) of no more than 30 $kg/m^2$.

4. The method according to claim 1, wherein the semaglutide is administered for at least 30 months.

5. The method according to claim 1, wherein the semaglutide is administered in a pharmaceutical composition comprising about 0.1-20 mg/ml semaglutide, about 2-15 mM phosphate buffer, about 2-25 mg/ml propylene glycol, about 1-18 mg/ml phenol, and has a pH in the range of 7.0-9.0.

6. The method according to claim 5, wherein the semaglutide is administered in a pharmaceutical composition comprising about 1.34 mg/ml semaglutide, about 1.42 mg/ml disodium phosphate dihydrate, about 14.0 mg/ml propylene glycol, about 5.5 mg/ml phenol, and has pH of about 7.4.

7. The method according to claim 6, wherein the semaglutide is administrated in a pharmaceutical composition comprising 1.34 mg/ml semaglutide, 1.42 mg/ml disodium phosphate dihydrate, 14.0 mg/ml propylene glycol, 5.5 mg/ml phenol, and has a pH of 7.4.

8. A method of reducing the risk of a major adverse cardiovascular event (MACE) in a subject in need thereof, wherein the method comprises administering to the subject a pharmaceutical composition comprising semaglutide in an amount of 0.05-2.0 mg once weekly by subcutaneous injection; wherein the subject has type 2 diabetes and cardiovascular disease;

wherein the MACE is selected from the group consisting of CV death, non-fatal MI, and non-fatal stroke; and wherein the cardiovascular disease is selected from the group consisting of prior myocardial infarction; prior stroke or transient ischaemic attack; prior coronary, carotid, or peripheral arterial revascularization; >50% stenosis on angiography or imaging of coronary, carotid, or lower extremity arteries; history of symptomatic coronary heart disease; asymptomatic cardiac ischemia; heart failure; and chronic renal impairment by estimated glomerular filtration rate<60 mL/min/1.73 $m^2$ per MDRD.

9. The method according to claim 8, wherein the subject has a BMI of no more than 30 $kg/m^2$.

10. The method according to claim 8, wherein the semaglutide is administered for at least 30 months.

11. The method according to claim 8, wherein the semaglutide is administered in a pharmaceutical composition comprising about 0.1-20 mg/ml semaglutide, about 2-15 mM phosphate buffer, about 2-25 mg/ml propylene glycol, about 1-18 mg/ml phenol, and has a pH in the range of 7.0-9.0.

12. The method according to claim 11, wherein the semaglutide is administered in a pharmaceutical composition comprising about 1.34 mg/ml semaglutide, about 1.42 mg/ml disodium phosphate dihydrate, about 14.0 mg/ml propylene glycol, about 5.5 mg/ml phenol, and has pH of about 7.4.

13. The method according to claim 12, wherein the semaglutide is administrated in a pharmaceutical composition comprising 1.34 mg/ml semaglutide, 1.42 mg/ml disodium phosphate dihydrate, 14.0 mg/ml propylene glycol, 5.5 mg/ml phenol, and has a pH of 7.4.

* * * * *